United States Patent [19]

Smith, Jr.

[11] Patent Number: 5,399,343
[45] Date of Patent: Mar. 21, 1995

[54] BIOCIDAL COSMETIC COMPOSITIONS

[75] Inventor: W. Novis Smith, Jr., Philadelphia, Pa.

[73] Assignee: Dr. W. Novis Smith and Company, Inc., Philadelphia, Pa.

[21] Appl. No.: 750,425

[22] Filed: Aug. 14, 1991

Related U.S. Application Data

[63] Continuation of Ser. No. 530,349, May 30, 1990, abandoned.

[51] Int. Cl.$^6$ .................................................. A61K 7/04
[52] U.S. Cl. .................................... 424/61; 424/78.02; 424/78.38; 424/401; 523/122
[58] Field of Search .................. 424/405, 401, 61, 69, 424/76.8, 79, 78.02, 78.38; 523/122

[56] References Cited

U.S. PATENT DOCUMENTS

| | | | |
|---|---|---|---|
| 3,865,619 | 2/1975 | Pennewiss | 428/412 |
| 4,000,317 | 12/1976 | Menda | 424/357 |
| 4,758,595 | 7/1988 | Ogunbiyi | 424/78 |
| 4,820,509 | 4/1989 | Yamazaki | 424/61 |
| 4,839,166 | 6/1989 | Grollier | 424/71 |
| 4,999,386 | 3/1991 | Oakes | 523/122 |
| 5,049,383 | 9/1991 | Huth | 424/78 |

FOREIGN PATENT DOCUMENTS 64-22824  1/1989  Japan .

*Primary Examiner*—Gollamundi S. Kishore
*Attorney, Agent, or Firm*—John Lezdey

[57] ABSTRACT

A cosmetic or body composition containing an effective amount of a non-leachable anti-microbial polymer. The polymer contains carboxyl groups which are at least partially neutralized or exchanged with anti-microbial quaternary ammonium cations or anti-microbial polyamides.

7 Claims, No Drawings

BIOCIDAL COSMETIC COMPOSITIONS

This is a continuation of application Ser. No. 530,349, filed May 30, 1990, now abandoned.

FIELD OF THE INVENTION

The present invention is concerned with cosmetic and body preparations containing non-leachable and non-absorbable anti-microbial polymers. More particularly, the invention relates to cosmetic and body preparation which contain anti-microbial polymers comprising polymers having carboxyl groups which are wholly or partially neutralized or exchanged with quaternary ammonium cations or polyamines possessing anti-microbial activity.

BACKGROUND OF THE INVENTION

There is a need in the cosmetic industry to provide a means for preventing fungal and/or bacterial growth in cosmetic and other body preparation which has no adverse effects on the user. There is a further need to provide body preparations which will inhibit the growth of odor causing bacteria and fungus.

It is known that extended wear of fingernail coatings can lead to fungal growth which can effect the wearer. However, there has not been found any effective means for combatting the fungal growth in a fingernail polish composition which does not yield another health hazard to the user.

It is further known that cosmetic compositions, such as lipstick and eye make-up provide a good environment for bacterial growth which is aided by its method of application. Prior to the present invention there has not been any means for combatting bacteria which is safe and effective and also compatible with cosmetic formulations.

Previously, hexachlorophene was widely used in many cosmetic and body preparations to kill bacteria on contact and to prevent growth of bacteria and fungus. Hexachlorophene was included in deodorant compositions, talcum preparations, foot powders, lipsticks, and the like. However, the hexachlorophene was used in direct contact with skin and was absorbable. Prolonged exposure to hexachlorophene was considered as being hazardous so that it was withdrawn from use in such compositions.

The bacteriostatic agents which are presently being utilized by the cosmetic industry such as 3-(trifluoromethyl)-4, 4'-dichlorocarbanilide (IRGASAN) and 5-chloro-2-(2,4-dichlorophenoxy) phenol (IRGASAN DP-300) of Ciba-Geigy cannot be utilized in hyperallergenic cosmetic formulations since there is the possibility of irritation over extended use. The compounds while insoluble in water are soluble in alkaline solutions and in organic solvents so that the compounds can be leached out of the composition. Moreover, these compounds have no film forming capabilities so that they cannot be effectively utilized in nail polishes and the like without adverse effects on the film forming properties of the compositions. Additionally, bacteriostatic agents merely prevent the growth of existing organisms and do not kill on contact new microorganisms which may be introduced into the compositions.

There is a need to provide hyperallergenic cosmetic compositions with a means for preventing bacterial and fungal growth which does not adversely affect the user.

Japanese Patent Publication No. 1989-22824, discloses a medicament for external use that is fungicidal and exhibits an antibacterial spectrum. The medicament comprises quaternary ammonium salts of polymeric carboxylic acid compounds which are sparingly soluble in water. However, the active component is utilized for its ability to permeate into the cutaneous stratum corneum so that such use cannot be continuous and without medical supervision.

The polymeric medicaments disclosed in the Japanese publication can be used in the present invention through the modification of the polymers with a suitable crosslinking agent as now proposed which insolubilizes the polymer-quaternary ammonium compound in the environment utilized but still provides the kill on contact of the microorganisms.

U.S. Pat. No. 4,332,763 to Hempel et al discloses the use of a quaternary ammonium polymer obtained by the reaction of dimethyl sulphate with a mixed polymer of vinyl pyrrolidone and dimethylamino ethylmethacrylate. However, the quaternary ammonium cation of this polymer is leachable and the polymer is slightly soluble so that polymer cannot be used in cosmetic compositions.

U.S. Pat. No. 3,872,128 to Byck, which is herein incorporated by reference, discloses anti-microbial ammonium polymer salts which are prepared from carboxyl-containing α-olefin polymers and quaternary ammonium salts. The polymers are used to form polymeric articles for hospitals and patient care.

U.S. Pat. No. 3,404,134 to Rees, which is herein incorporated by reference discloses a process for crosslinking copolymers of alpha olefin and alpha, beta ethylenically unsaturated carboxylic acid units. The copolymers are crosslinked utilizing diamine cations. None of the diamine cations are stated as being anti-microbial. Furthermore, the polymers are used to make molded articles and sheet material.

U.S. Pat. Nos. 3,488,215 and 3,865,619, which are herein incorporated by reference, disclose swollen or swellable hydrophilic resins that can be crosslinked with select quaternary ammonium salts and used in the present invention.

It is understood that the term "polymer-quat" as used herein means polymers which are wholly or partially neutralized with biocidally active quaternary ammonium compounds or polyamine such as by ionic bonding or crosslinking whereby the biocidal activity of the quaternary ammonium compound or amine is maintained.

The term "body composition or preparation" used herein relates to powders, lotions, salves, or the like used in treating the body such as food powders, talcum preparations, deodorant preparations, baby preparations and the like.

SUMMARY OF THE INVENTION

In accordance with the present invention there is provided a means for destroying and/or inhibiting the growth of microorganisms in cosmetic and body preparations by incorporating therein an effective amount of a non-leachable non-absorbable anti-microbial polymer containing carboxyl groups which are at least partially neutralized or exchanged with anti-microbial quaternary ammonium cations or polyamines.

Advantageously, the anti-microbial polymer is crosslinked to adjust its solubility according to the compositions in which it is used. The crosslinking can be reversible or irreversible so that the polymer can be solubilized or insolubilized before or after formulation.

The polymer-quats can be used directly in existing cosmetic compositions, baby lotions, hand creams and the like as potential fungicides, bactericides, and in general, anti-microbials. The killing power or attenuation power is dependent upon the particular anti-microbial quaternary ammonium compound or amine compound which is utilized. The solubility of these polymer-quats in aqueous and organic solvents can be modified by the addition of crosslinking agents, for example ammonium, sodium, magnesium, calcium or aluminum cations, or the use of diquaternary compounds. The amount of crosslinking will affect the solubility of the polymer-quats. The nature of the quaternary amine cation, the extent of neutralization and the amount of quaternary amine cation per polymer chain, and the nature of the comonomer with the carboxyl containing group will affect the solubility of the polymer-quats. Therefore, these factors can be adjusted so that the polymer-quat is soluble only in the aqueous phase of a cream or cosmetic, or is soluble only in the organic phase or in both phases. In addition, the nature of the polymer-quat can be adjusted to lie on the surface of the skin without penetration or causing irritation.

DESCRIPTION OF THE PREFERRED EMBODIMENTS

In accordance with one embodiment of the invention the anti-microbial polymer-quats are formed in a continuous phase, that is, solubilized or at least swollen either in water, an organic phase or a mixed organic and water phase by the reaction of a biocidal quaternary ammonium salt with a carboxyl-containing polymer. After formation of the polymer-quat, the solubility of the polymer-quat is adjusted with suitable crosslinking agents prior to formulation into the cosmetic or body composition, after formulation or upon contact with the skin. In some cases there is no need for adjustment because the solubility is proper for the formulation and contemplated use.

These polymer-quats are unique in that they are formed from polymers which are initially solubilized or totally swollen by the solvent. They can then be tailored in their solubility to be soluble or insoluble in different phases of the formulations. These polymer-quats can be reversibly or irreversibly crosslinked to modify there reactivity and solubility in various applications.

Hydrophilic polymer-quats that can be swollen are disclosed in U.S. Pat. No. 3,865,619. These polymer-quats comprise:

(a) about 12 to 30 percent by weight of an ethylenically unsaturated polymerizable monomer having a salt forming or salt group therein;

(b) about 40 to 88 percent by weight of at least one alkanol ester of acrylic acid and/or methacrylic acid, said esters having from 1–4 carbon atoms in the alcohol portion thereof.

The monomers of Part (a) having salt groups can either be salts of polymerizable carboxylic acid, salts of polymerizable amines, or quaternary ammonium salts. Preferred materials include the salts of α, β-unsaturated aliphatic mono- and di-carboxylic acids, particularly salts of those acids having 3–5 carbon atoms, such as salts of acrylic acid, methacrylic acid, maleic acid, fumaric acid, and itaconic acid. Salts of half-esters of the aforementioned dicarboxylic acids, particularly of esters formed with $C_{1-8}$ alkanols, as well as salts of vinyl sulfonic acids or of methacryl taurines are suitable. Salts of acrylic acid and methacrylic acid are preferred.

As cations for solubilizing the polymers, those of the alkali metals are preferred, as well as those of the alkaline earth metals, of amines such as trimethylamine, tributylamine, mono-, di-, and tri-ethanolamine, and diethylamine, or of ammonium and alkyl-ammonium.

In accordance with a second embodiment of the invention the anti-microbial polymer-quats of the invention are prepared with a water soluble polymer, namely one which has been neutralized with sodium ions and treated with an anti-microbial quaternary amine salt. The sodium salt is then washed from the gelled or less soluble polymer-quaternary salt complex which separates. Alternatively, the complex may be formed by reacting a quaternary amine acetate with the free carboxyl groups of the polymer and removing the acetic acid which is formed.

The solubility of the polymer-quats of the invention can be adjusted by utilizing suitable quaternary ammonium salt reactants, crosslinking with diquaternary ammonium compounds; suitable polyamines, alkali or alkaline earth cations, or the like. Some of these crosslinking techniques are discussed in the aforementioned patents.

The copolymers which may be used in preparing the polymer-quats of the second embodiment of the present invention comprise at least one alpha olefin unit having the general formula:

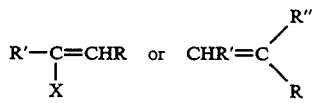

wherein R, R' and R" each represent a radical selected from the class consisting of hydrogen and hydrocarbyl radicals having one to eight carbon atoms and at least one alpha, beta ethylenically unsaturated carboxylic acid unit having one to two carboxylic acid groups, and X represents —OR, COOR, CN or phenyl. Preferably, the alpha, beta ethylenically unsaturated carboxylic acid unit has 3 to 8 carbon atoms.

Specific alpha olefin units useful in the copolymers include: ethylene, propylene, butene-1, styrene, pentene-1, hexene-1, heptene-1, 3 methylbutene-1, styrene, pentene-1, hexene-1, and heptene-1.

Units useful in the copolymers include: acrylic, methacrylic, ethacrylic, itaconic, maleic, fumaric, monoesters of dicarboxylic acid such as ethyl hydrogen fumarate, maleic anhydride, ethyl hydrogen maleate, vinyl alcohol, vinyl chloride, vinyl acetate and vinyl ethers. Maleic anhydride and other alpha, beta ethylenically unsaturated anhydrides are considered acids for the purposes of the present invention.

Additionally, any third copolymerizable monomer can be employed in combination with the olefin and the carboxylic acid comonomer. Preferred termonomers are vinyl esters are acrylates, i.e., alkyl acrylates and methacrylates having up to eight carbon atoms, such as vinyl acetate, vinyl propinate, methyl methacrylate and ethyl acrylate. The scope of base copolymers suitable for use in the present invention is illustrated by the following examples which include high and low molecular weight polymers:

Ethylene/acrylic acid copolymers, ethylene/methacrylic acid copolymers, ethylene/itaconic acid copolymers, ethylene/methyl hydrogen maleate copolymers, ethylene/maleic acid copolymers, ethylene/acrylic acid/methyl methacrylate copolymers, ethylene/methacrylic acid/methyl methacrylate copolymers, ethylene/itaconic acid/methyl methacrylate copolymers, ethylene/methyl hydrogen maleate/ethyl acrylate copolymers, ethylene/methacrylic acid/vinyl acetate copolymers, ethylene/acrylic acid/vinyl alcohol copolymers, ethylene/propylene acrylic acid copolymers, ethylene/styrene acrylic acid copolymers, ethylene/methacrylic acid/acrylonitrile copolymers, ethylene/fumaric acid/vinyl methyl ether copolymers, ethylene/vinyl chloride/acrylic acid copolymers, ethylene/vinylidene chloride/acrylic acid copolymers, ethylene/vinyl fluoride/methacrylic acid copolymers, ethylene/chlorotrifluoroethylene/methacrylic acid copolymers, ethylene/methacrylic acid/acrylic acid copolymers, ethylene/maleic acid or anhydride copolymers, and ethylene/methacrylic acid/maleic anhydride copolymers.

Other suitable polymers include carboxyl cellulose, low molecular weight styrene/maleic acid or anhydride copolymers, polyacrylic acid, polymethacrylic acid, copolymers of vinyl ether and maleic anhydride, condensation acids from oleic acid, linoleic acid, and the like.

The cations used in adjusting the solubility of the polymer can be supplied as water soluble salts. The cations should have an effective valence of one to three. The term "effective valence" as used herein means that the cation forming material is readily ionized to form cations having a valence in the range of one to three, but that the cation forming material is not readily ionized to form cations having more than three valence charges; in other words, the cation is complexed to such an extent that the number of ionic charges is in every case in the range of 1 to 3. The preferred complexed metal ions are those in which all but one of the metal valences are complexed and one is readily ionized. Such compounds are in particular the mixed salts of very weak acids, such as oleic and stearic acid, with ionizable acids, such as formic and acetic acid.

The uncomplexed metal ions which are suitable for use in the process of the present invention comprise mono-, di- and trivalent ions of metals in Groups I, II, III, IV-A and VIII of the Periodic Table of Elements (see page 392, Handbook of Chemistry and Physics, Chemical Rubber Publishing Co., 37th ed.). Uncomplexed monovalent metal ions of the metals in the stated groups are also suitable in forming the ionic copolymers of the present invention with copolymers of olefins and ethylenically unsaturated, dicarboxylic acids. Suitable monovalent metal ions are $Na^+$, $K^+$, $Li^+$, $Cs^+$, $Ag^+$, $Hg^+$, and $Cu^+$. Suitable divalent metal ions are $Be^{+2}$, $Mg^{+2}$, $Ca^{+2}$, $Sr^{+2}$, $Ba^{+2}$, $Cu^{+2}$, $Cd^{+2}$, $Hg^{+2}$, $Sn^{+2}$, $Pb^{+2}$, $Fe^{+2}$, $Co^{+2}$, $Ni^{+2}$, and $Zn^{+2}$. Suitable trivalent metal ions are $Al^{+3}$, $SC^{+3}$, $Fe^{+3}$, and $Y^{+3}$.

The complexed metal ions which are suitable for use in the process of the present invention are di, tri, tetra and hexavalent ions that have been complexed so that their effective valence is within the range of 1 to 3, preferably 1. Suitable metal ions are the divalent and trivalent ions listed above, tetravalent ions such as $Ti^{+4}$, $Zr^{+4}$, $Hf^{+4}$, $V^{+4}$, $Ta^{+4}$, $W^{+4}$ and hexavalent ions such as $Cr^{+6}$, $Ce^{+6}$, and $Fe^{+6}$. Suitable complexing agents include stearate, oleate, salicylate, and phenolate radicals.

The metallic cations can be added to the copolymer in the form of salts, oxides, hydroxide, carbonate, free metal, metal hydride, metal alkoxide or organometallic compounds. If the metallic cation producing material is readily soluble in water at the reaction conditions, a considerable degree of reaction between metallic ions and the carboxyl groups will take place. The equilibrium of the reaction can be shifted to favor this reaction by removal of the anionic portion of the cation producing material as soon as it has become associated with the acid hydrogen. If the cation producing material is the salt of a very weak acid such as sodium resorcinol, the equilibrium of the reaction is sufficiently in favor of the formation of the ion links, and no steps need to be taken to remove the anionic portion of the cation producing material from the copolymer.

If the new salt of the cation is less soluble, the reaction will shift in favor of the new polymeric salt.

If the metallic cation producing material is substantially insoluble under the reaction conditions, it is desirable to convert the insoluble material into a soluble or slightly soluble one in situ to accelerate the reaction. This may be readily accomplished in the case of metal oxides, hydroxides and carbonates by the addition of acid such as acetic acid, lactic acid, propionic acid, and mixtures of these acids.

Some of the factors which cause "diaper rash" or "diaper dermatitis" include ammonia, bacteria, pH, candida albicans and moisture. Urine in contact with enzymes and bacteria breaks down into ammonia and causes odor. It therefore appears that diaper rash control may be achieved to some degree by eliminating or reducing the bacteria and enzymes which are present and those which promote the breakdown of urine. Accordingly, it is proposed to include in body preparations and powders which are intended for use infants and individuals suffering from incontinence the polymer-quats of the invention in order to reduce and control the growth of the bacteria and enzymes which may be present. A suitable body powder for infants and for adults to control odor comprises 20 to 40 parts by weight of talc, about 20 to 40 parts by weight of a buffer, preferably sodium bicarbonate, about 10 to 20 parts by weight of polymer-quat and optionally, perfume.

Representative examples of suitable quaternary nitrogen-based anti-microbial agents include methylbenezalkonium chloride, benzalkonium chloride, dodecyltrimethyl ammonium bromide, tetradecyltrimethyl ammonium bromide and hexadecyltrimethyl ammonium bromide. Heterocyclic quaternary nitrogen-based anti-microbial agents include dodecylpyridinium chloride, tetradecylpyridinium chloride, cetylpyridinium chloride (CPC), N-alkyl pentamethyl propane diammonium dichloride, dicocodimethyl ammonium chloride, pyridinium salts, pyridinium salts, triazines such as DOWICIL sold by Dow Corning Corporation, tetradecyl-4-ethylpyridinium chloride and tetradecyl-4-methylpyridinium chloride.

Other suitable anti-microbial agents which may be used are disclosed in Kirk-Othmer; *Encyclopedia of Chemical Technology*, 3rd Ed. Vol. 7, 1979, pp 793-832.

In accordance with a still further embodiment of the invention, there is provided a film forming anti-microbial polymer which can be incorporated into existing cosmetic setting lotions and lacquers, such as, for example, nail polish. In some cases, the polymer-quat of the invention can be used in place of a polymer of the composition. Typical nail polish formulation in which the polymer-quat can be incorporated are disclosed in U.S. Pat. Nos. 4,289,752; 4,032,628 and 3,925,287, which are herein incorporated by reference. Generally, an amount of about 0.5 to 5% by weight of solids in the composition is sufficient to prevent growth of fungi.

The polymer-quats of the invention can be generally prepared as follows:

A solution of the polymer in water or water-alcohol is formed either as the ammonium or sodium salt with ammonium or sodium hydroxide, respectively. The anti-microbial compound is dissolved in water or a water soluble solvent if possible. The molecular ratio of anti-microbial compound to sodium or ammonium carboxylate groups in the polymer or mixture of polymers is adjusted to one or less than one by varying the quantity of solution to be added to the polymer solution. The appropriate amounts of the two solutions are mixed with stirring forming a fine precipitate. After about an hour the precipitate is filtered off and dried. This polymer quat is used for adding directly into skin lotions, cosmetics, herbicides, etc. for control and the killing of microorganisms to increase the shelf life of the cosmetics.

If the solubility of the polymer-quat is too high, it can be adjusted or modified by the addition of di-or polyquaternary ammonium salts which serves to crosslink the polymer chains causing the polymer-quat to be more insoluble. The addition of polyvalent cations such as calcium, magnesium, aluminum, etc. will also cause the polymer chains to associate or crosslink and become more insoluble. The addition of polyamines also will cause this reversible crosslinking.

The preparation of the polymer-quats generally follow the following reactions:

$$yQ^+X^- + POLYMER(COO^-M^+)_y \rightarrow POLYMER(CO^-Q^+)_y + M^+X^- \quad 1)$$

wherein
M=Na, ammonium, K, Li, etc.
X=Cl, acetate, Br, etc.
y=1 or more, preferably 1-2
Q=a quaternary compound or polyamine

$$yQ' + POLYMER(COOH)_y \rightarrow POLYMER(COO^-H^+Q)_y \quad 2)$$

$$yH^+Q^{-"} + POLYMER(COO^-HN^+RR'-NR'R'-)_y \rightarrow POLYMER(COO^{-HN}+RR'-NRR'H^+Q) \quad 3)$$

$$yH^+Q^{-"} + POLYMER(NRR')_y \rightarrow POLYMER(NRR'H^+Q^-)_y \quad 4)$$

wherein R, R' and R"=hydrogen, alkyl, alkenyl, etc.

Conventional high shear grinding procedures can be used to form the pigment containing cosmetic preparations with the polymer-quats of the invention. Typical procedures that are used are sand grinding, ball milling, pebble milling, attritor grinding, high shear mixing and the like. For pigments which are difficult to disperse, a two roll mill technique is used. Typical pigments of this type are iron oxide pigments, irgazin yellows, and the like. In a typical two-roll mill process, is mixture is prepared from the pigment and a solution of the polymer-quat and charged onto a two roll mill in which one roll is heated to 75°-150° C. and the other is about room temperature. The mixture is milled until a uniform dispersion is formed. This can be blended with other cosmetic ingredients to form a mill base.

The following examples are illustrative of the invention but are not to be construed as to limiting the scope thereof in any manner. The percentages disclosed herein relate to percentages by weight unless otherwise stated.

EXAMPLE 1

A. Preparation of copolymer:

| Ingredients | % by weight |
|---|---|
| Methyl methacrylate | 40 |
| Styrene | 10 |
| N-butylacrylate | 16 |
| Methacrylic acid | 34 |

The ingredients are mixed in 120 parts of ethanol and 280 parts of dioxane using 1.5 parts of tert.butyl peroctate.

B. The polymer solution of Part A is then neutralized with a 1 percent solution of sodium hydroxide and filtered. The white filtrate is then stirred in an aqueous solution of 10% dimethyldidecylammonium chloride for two hours. The resulting mixture is cooled and filtered to yield a powder of swollen methylmethacrylate n-butylacrylate/styrene ionically bonded and swollen with the dimethyldidecy ammonium compound.

C. Test

An antibacterial spectrum was measured in the following manner.

To a 500 ml-Erlenmeyer flask which was placed in a constant temperature bath of 30° C. equipped with a shaker was added 20 mg. of polymer-quat of Part B. To the flask was added 100 ml of bacteria suspension listed in Table 1 ($6 \times 10^8$ cells of bacteria) of 30° C. and the mixture was shaked immediately. Each 1 ml. of the mixture was sampled 0, 2 and 5 minutes after the addition of the bacteria suspension. The sample was immediately diluted with sterile isotonic sodium chloride solution in 10, 100 and 100 times in dilution rate and then spread on nutrient agar plates.

Survival rate (%) was determined by measuring the survived bacteria in the colony after cultivation at 37° C. for 24 hours.

The results are given in Table 1.

TABLE 1

| Bacteria | Survival rate (%) after 2 min. | Survival rate (%) after 5 min. |
|---|---|---|
| Staphylococcus aureus (ATCC6538) | 0 | 0 |
| Salmonella choleraesius (ATCC10708) | 0 | 0 |
| Brevibacterium ammoigenes (ATCC6871) | 0 | 0 |
| Proteus Vulgaris (ATCC8427) | 30.5 | 5 |

EXAMPLE 2

An aqueous solution of didecyl dimethyl ammonium chloride was added slowly with stirring to an aqueous solution of sodium carboxymethyl cellulose. The molecular amount of anti-microbial was approximately 0.8 ratio to the amount of neutralized carboxyl groups present in the polymer. The resultant slurry was stirred for one hour and filtered and the recovered solid dried. The solid polymer-quat was used directly in formulations as an anti-microbial compound.

EXAMPLE 3

A solution of Adogen 477 (a diquaternary chloride) namely, N-fallow pentamethyl propane diammonium dichloride in water was added to an aqueous solution of low molecular weight polyacrylic acid (as the ammonium salt) with vigorous stirring. The molecular amount of anti-microbial was approximately 0.8 ratio to the amount of neutralized carboxyl groups present in the polymer. The precipitate was filtered and dried. It was useful as a anti-microbial formulating agent.

EXAMPLE 4

A solution of low molecular weight copolymer of ethylene/acrylic acid as the ammonium salt was added to a solution of BIOBAN P-1487 which is a mixture of substituted morpholines having as the principal ingredient 4-(2-nitrobutylmorpholine). About 4% of a 5% solution of calcium chloride was then added to ensure total precipitation and insolubilization of the polymer-quat. The molecular amount of anti-microbial was approximately 0.8 ratio to the amount of neutralized carboxyl-groups present in the polymer. The precipitate was recovered and used as an anti-microbial agent in formulations.

EXAMPLE 5

MAKE-UP FOUNDATION

| Ingredient | % by weight |
|---|---|
| Polymer-quat of Example 2 | 5.0 |
| Isopropyl lanolate | 4.0 |
| Stearic Acid | 2.6 |
| Self-emulsifiable glycol stearate | 5.0 |
| Cosmetic oil | 20.0 |
| Sodium lauryl sulfate | 1.1 |
| Bentonite | 2.5 |
| Perfume | qs |
| Demineralized water | qs 100 |
| Additives: | |
| Titanium oxide | qs according to shades |
| Iron oxide | and covering |
| Talc | powder desired |

EXAMPLE 6

BODY POWDER OR BABY POWDER

| Ingredient | % by weight |
|---|---|
| Talc | 40 |
| Sodium bicarbonate | 40 |
| Polymer-quat of Example 3 | 20 |

As a body powder the composition is effective to deactivate or kill odor causing bacteria. As a baby powder the sodium bicarbonate neutralizes the pH of urine and the polymer-quat kills the odor causing bacteria in the urine.

EXAMPLE 7

A nail polish is prepared according to the invention by mixing the following ingredients.

A. Base Varnish

| Ingredient | % by weight |
|---|---|
| Nitrocellulose | 14 |
| Camphor | 2 |
| Butyl phthalate | 5 |
| Ethyl alcohol | 4 |
| Butyl alcohol | 4 |
| Toluene | 20 |
| Ethyl acetate | 15 |
| Butyl acetate | 32 |
| Carboxy cellulose - didecyldimethyl Ammonium polymer-quat | 4 |

The polymer-quat can be replaced by any other film forming polymer-quat of the invention.

B. The base varnish can be used to obtain a polish for coloring nails by admixing thereto certain dyes and an antisediment mixture:

| Antisediment mixture | |
|---|---|
| Bentone | 1.20 g |
| Phosphoric | 0.02 g |
| Dyes: | |
| Titanium oxide | 1 g |
| D and C Red 7 | 0.4 g |
| D and C Red 11 | 0.3 g |
| D and C Red 5 | 0.2 g |
| D and C Yellow 5 | 0.6 g |

What is claimed is:

1. In a nail lacquer composition comprising a base varnish of film forming members, the improvement which comprises the inclusion therein of an antifungal effective amount of an anti-microbial film forming polymer consisting of a carboxyl cellulose neutralized, with an anti-microbial quaternary ammonium cation, whereby said quaternary ammonium cation is not leachable with water and lies on the skin without penetration.

2. The nail lacquer composition of claim 1 wherein said anti-microbial polymer is present in an amount of about 0.5 to 5% by weight of solids in said composition.

3. The nail lacquer composition of claim 1 wherein said base varnish contains nitrocellulose.

4. The nail lacquer composition of claim 1 wherein said quaternary ammonium cation is selected from the group consisting of cetyl pyridinium, benzalkonium, dodecyltrimethyl ammonium, tetradecyltrimethyl ammonium and didecyl dimethyl ammonium.

5. The nail lacquer of claim 1 wherein said polymer is sodium carboxymethyl cellulose and said quaternary ammonium cation is didecyldimethyl ammonium.

6. The nail lacquer of claim 1 including a coloring agent.

7. A film forming antimicrobial complex consisting of a carboxyl cellulose neutralized with an anti-microbial quaternary ammonium cation.

* * * * *